United States Patent
Mayes et al.

(10) Patent No.: US 6,207,749 B1
(45) Date of Patent: Mar. 27, 2001

(54) COMB COPOLYMERS FOR REGULATING CELL-SURFACE INTERACTIONS

(75) Inventors: Anne M. Mayes, Waltham; Linda G. Griffith; Darrell J. Irvine, both of Cambridge; Pallab Banerjee, Boston; Terry D. Johnson, Allston, all of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/634,095

(22) Filed: Aug. 8, 2000

Related U.S. Application Data

(62) Division of application No. 09/290,140, filed on Apr. 13, 1999.
(60) Provisional application No. 60/081,596, filed on Apr. 13, 1998.

(51) Int. Cl.[7] .................................................. C08J 5/24
(52) U.S. Cl. ............................ 524/731; 524/732; 427/2.1; 427/2.12; 427/2.13; 435/373; 435/374; 435/375; 435/378; 435/402
(58) Field of Search ............................ 524/731, 732; 427/2.1, 2.12, 2.13; 435/373, 374, 375, 378, 402

(56) References Cited

FOREIGN PATENT DOCUMENTS

| 197 06 667 A1 | 8/1998 | (DE) . |
|---|---|---|
| 97/06833 A1 | 2/1997 | (WO) . |
| 98/12228 A1 | 3/1998 | (WO) . |
| 99/52560 A1 | 10/1999 | (WO) . |

OTHER PUBLICATIONS

Ando, et al, "Activation of protein kinase C inhibits human keratinocyte migration," *J. Cell Physiol.* 156:487–496 (1993).
Barrett, "Dispersion polymerisation in organic media," *Brit. Polym. J.* 5:259–271 (1973).
Chen, et al, "Geometric control of cell life and death," *Science* 276:1425–1428 (1997).
Clark & Brugge, "Integrins and signals transduction pathways: the road taken," *Science* 268: 233–239 (1995).
De Gennes, *Scaling Concepts in Polymer Physics*, Cornell University Press: Ithaca, NY, 1979.
DiMilla, et al, "Maximal migration of human smooth muscle cells on fibronectin and type IV collagen occurs at an intermediate attachment strength," *J. Cell Biol.* 122:729–737 (1993).
Hern & Hubbell, "Incorporation of adhesion peptides into nonadhesive hydrogels useful for tissue resurfacing," *J. Biomed. Mater. Res.* 39:266–276 (1998).
Hynes, "Integrins: a family of cell surface receptors," *Cell* 48:549–554 (1987).

Imanishi, "N–Carboxyanhydride" in *Ring–Opening Polymerization*, vol. 2, Chapter 8., (Ivin, et al., eds.), Elsevier: London, 1984.

Irvine, et al., "Comparison of tethered star and linear poly(ethylene oxide) for control of biomaterials surface properties," *J. Biomed. Mater. Res.* 40:498–509 (1998).

Kornberg, et al, "Signal transduction by integrins: increased protein tyrosine phosphorylation caused by clustering of beta 1 integrins," *Proc. Natl. Acad. Sci. USA* 88:8392–8396 (1991).

Kricheldorf, α–*Aminoacid–N–Carboxy–Anhydrides and Related Heterocycles*, Springer–Verlag: Berlin, 1987.

Kricheldorf, "Polypeptides". in *Models of Biopolymers by Ring–Opening Polymerization*, (Penczek, ed.) Chapter 1, CRC Press:Boca Raton, 1990.

Kuhl & Griffith–CIMA, "Tethered epidermal growth factor as a paradigm for growth factor–induced stimulation from the solid phase," *Nat Med* 2(9):1022–7 (1996).

(List continued on next page.)

*Primary Examiner*—Nathan M. Nutter
(74) *Attorney, Agent, or Firm*—Arnall Golden & Gregory, LLP

(57) ABSTRACT

Synthetic comb copolymers which elicit controlled cellular response, methods of applying these polymers to various surfaces, and methods of using the polymers for modifying biomaterial surfaces, in tissue engineering applications and as drug delivery devices are provided. The comb copolymers are comprised of hydrophobic polymer backbones and hydrophilic, non-cell binding side chains which can be end-capped with cell-signaling ligands that guide cellular response. By mixing non-cell binding combs with ligand-bearing combs, the surface concentration and spatial distribution of one or more types of ligands, including adhesion peptides and growth factors, can be tuned on a surface to achieve desired cellular response. In one embodiment, the combs are used as stabilizing agents for dispersion polymerization of latexes. The comb-stabilized latexes can be applied to substrates by standard coating operations to create a bioregulating surface, or used as drug delivery agents. In another embodiment, the combs can be blended in small quantities to a hydrophobic matrix polymer and processed to affect the surface segregation of the comb. The comb copolymers are formed in one embodiment by providing a biodegradable polyester backbone that includes reactive groups, and reacting the reactive groups in the backbone with reactive chain ends on a low molecular weight hydrophilic polymer. In another embodiment, non-biodegradable comb copolymers are formed by free radical synthesis of a hydrophobic monomer and a hydrophilic macromonomer. In all of the above embodiments, a portion of the hydrophilic polymer side chains can be covalently coupled to cell-signaling ligands such as adhesion peptides or growth factors to control cellular response.

16 Claims, No Drawings

OTHER PUBLICATIONS

Massia & Hubbell, "An RGD spacing of 440 nm is sufficient for integrin alpha V beta 3–mediated fibroblast spreading and 140 nm for focal contact and stress fiber formation," *J. Cell Biol.* 114:1089–1100 (1991).

Miyamoto, et al, "Integrins can collaborate with growth factors for phosphorylation of receptor tyrosine kinases and MAP kinase activation: roles of integrin aggregation and occupancy of receptors," *J. Cell Biol.* 135:1633–1642 (1996).

Ober, "Dispersion copolymerization in non–aqueous media," Makromol. Chem. Macromol. Symp. 35/36:87–104 (1990).

Ober, et al., "Monodispersed, micron–sized polystyrene particles by dispersion polymerization," *J. Polym. Sci., Polym. Lett. Ed.* 23:103–108 (1985).

Paine, et al., "Dispersion polymerization of styrene in polar solvents. 6. Influence of reaction parameters on particle size and molecular weight in Poly (N–vinylpyrrolidone)–stabilized reactions," *Macromolecules* 23:3104–3109 (1990).

Park, et al., "Integration of surface modification and 3D fabrication techniques to prepare patterned poly(L–lactide) substrates allowing regionally selective cell adhesion," *J. Biomater. Sci. Polym. Ed.* 9:89–110 (1998).

Plopper, et al, "Convergence of integrin and growth factor receptor signaling pathways within the focal adhesion complex," *Mol. Biol. Cell* 6:1349–1365 (1995).

Rouslahti, "RGD and other recognition sequences for integrins," *Ann.Rev. Cell. Dev. Biol.* 12: 697–715 (1996).

Shen, et al., "Control of particle size in dispersion polymerization of methyl methacrylate," *J. Polym. Sci., Polym. Chem. Ed.* 31:1393–1402 (1993).

Warson, *The Applications of Synthetic Resin Emulsions*, Benn: London, 1972.

Welsh, et al, "A negative feedback loop attenuates EGF–induced morphological changes," *J. Cell. Biol.* 114:533–543 (1991).

COMB COPOLYMERS FOR REGULATING CELL-SURFACE INTERACTIONS

This application is a divisional of U.S. application Ser. No.09/290,140 filed Apr. 13, 1999, which claims priority to U.S. Provisional Application Serial No. 60/081,596 filed Apr. 13,1998.

The United States government has certain rights in this invention by virtue of National Science Foundation grant No. DMR-9400334, OSP Project No.6227 to Anne M. Mayes, and National Science Foundation Grant No. BES 9632714 to L. G. Griffith.

BACKGROUND OF THE INVENTION

Polymeric materials that elicit controlled cell responses, and have good mechanical, optical and/or biodegradation properties, are disclosed for use in biomedical applications. Processing methods by which such polymers can be localized at a biomaterial surface are also disclosed.

Polymers currently in use for biomedical applications generally tend to be hydrophobic. As defined herein, hydrophobic refers to a material that repels water, i.e., exhibits a static contact angle with water greater than 60 degrees at 20° C., and has a water permeability P less than $3 \times 10^{-10}$ $cm^3(STP)$ cm/($cm^2$ s Pa). This can give rise to uncontrolled interactions between cells and adsorbed proteins at the surface of the material, which can result in a chronic inflammatory response that can lead to failure of implants and even promote tumorigenecity (Warson, The Applications of Synthetic Resin Emulsions, Benn, London (1972)). Metal or ceramic materials used in implant applications similarly can elicit undesirable cell responses.

For tissue engineering applications, it is essential that the polymeric material used to form a biodegradable scaffold for cells promote cell adhesion, migration, growth and differentiation while providing adequate structural support. Though commonly used synthetic scaffold materials such as poly(lactide), poly(glycolide), etc., and copolymers thereof, have suitable mechanical, processing and biodegradation properties, their hydrophobic nature leads to protein adsorption and denaturing on the material surface which elicits uncontrolled cell response.

The ideal surface for many biomaterials applications would resist protein adsorption while providing cells with specific chemical signals to guide adhesion, survival, growth, migration and differentiation. As used herein, the term "biomaterial" refers to a nonviable material used in a medical device intended to interact with biological systems. Polymer surfaces modified with poly(ethylene oxide) have been studied in recent years for the reduction of protein adsorption at the surface of biomaterials (Paine et al. *Macromolecules*, 23:3104 (1990)). The objective of these surface modification schemes is the elimination of nonspecific interactions of cells with implant materials. One way in which specific chemical signals can be relayed to cells at a surface is through tethered ligands for cell surface receptors (Barret, *Brit. Polym. J.* 5:259 (1973)). Delivery of signals in this manner has advantages over the addition of soluble factors, as the signal is presented in a very localized manner at a controlled dose without diffusive loss (Kuhl and Griffith, *Nature Medicine*, 2:1002 (1996)). In addition, tethered ligands may provide more constant stimulation to cells by avoiding the down-regulation present when soluble ligands are internalized by cells. Control over spatial distribution of ligands on surfaces may also be key to guiding cell behavior. Thus systems which will allow spatial control of local ligand density, or the creation of clusters of ligands on a surface, in addition to providing control over the average surface density of ligands, are highly desirable (Kornberg et al, *Proc. Natl. Acad. Sci. USA*, 88:8392 (1991)).

Integrins, dimeric adhesion receptors including one of approximately ten known alpha chains paired with one of approximately six known beta chains, mediate a wide range of interactions between cells and extracellular matrix (ECM) and control cell behaviors as diverse as migration, growth, and differentiation, providing a permissive environment for the action of growth factors. For many integrins, the specificity of integrin binding to matrix proteins has been mapped to small, discrete peptide domains and new sites continue to be elucidated (Rouslahti, *Ann. Rev. Cell. Dev. Biol.*, 12: 697 (1996); Hynes, *Cell*, 48:549 (1987)). The prototypical example of such specificity is the RGD site first identified in fibronectin and subsequently identified in other matrix proteins. The RGD peptide enables complete replacement of adhesive function of fibronectin for cells expressing certain integrins.

Much data supports the idea that both occupancy and clustering of integrins are required to elicit full cellular responses mediated by integrins (Clark and Brugge, *Science*, 268:233 (1995)). For example, fill EGFR activation of MAP kinase requires integrin clustering and occupancy (Miyamoto et al, *J. Cell Biol.*, 135:1633 (1996)). Thus, the spatial presentation of ligand in the environment, i.e., whether ligands are spaced closely enough to afford clustering of ligand-bound integrins, may influence cellular behaviors governed by integrins. Indeed, spacing of synthetic RGD ligand covalently linked to the substrate has been shown to have an influence on cell adhesion and spreading (Massia and Hubbell, *J. Cell Biol.*, 114:1089 (1991)). At the same time, the surface concentration of an adhesion ligand such as fibronectin has been shown to have a substantial influence on integrin-mediated behaviors such as migration (DiMilla et al,*J. Cell Biol.*, 122:729 (1993)). A recent study using self-assembled monolayers patterned in one micron adhesive/nonadhesive domains demonstrated the role of cell spreading and receptor occupancy on cell survival (Chen et al, *Science*, 276:1425 (1997). The length scale in that study was approximately that of a focal adhesion complex (or larger), but it is likely that clustering over much smaller length scales (3–10 integrins) is also physiologically relevant. Indeed, data suggests strongly that RGD clustering on the less than 100 nm length scale has profound effects on the integrin-mediated behavior of migration. Since both the concentration and spatial distribution of ligand influence cell response, it is desirable to have a means to vary these two parameters independently, and over a broad range of length scales (nanometers to micrometers), in order to guide cell response.

Integrins can initiate intracellular signaling cascades that overlap with those of growth factors such as epidermal growth factor (EGF). Cross-communication between adhesion and growth factor receptors may occur by direct physical association within the focal adhesions. Both types of receptors are concentrated in these structures (Miyamoto et al, *J. Cell Biol.*, 135:1633 (1996); Plopper et al, *Mol. Biol. Cell*, 6:1349 (1995)), and both receptors can stimulate some of the same down-stream effect on molecules such as MAP kinase. Close proximity of adhesion and growth factor receptors in the focal adhesion complex provides for a free flow of both positive and negative regulatory signals between the two. A number of signaling molecules have been proposed as forming this linkage; one intracellular mechanism of transmodulation is via protein kinase C (PKC)-mediated attenuation of the epidermal growth factor receptor (EGFR). It is also likely that PKC activity secondary to phospholipase $C_\gamma$ or phospholipase D activation by EGFR alters integrin-based substratum connections (Welsh et al, *J. Cell Biol.*, 114:533 (1991); Ando et al, *J. Cell. Physiol.*, 156:487 (1993)). It is thus desirable to have a method by which two or more types of signaling ligands, such as adhesion peptides and growth factors, can be simultaneously located at the surface of a biomaterial in controlled quanitity and spatial distribution.

To date, few if any model systems are able to meet both protein resistance and cell signaling surface requirements, while approaches using clinically-applicable materials have focused on hydrogels (Hern and Hubbell, *J. Biomed. Mater. Res.*, 39:266 (1998)), which have limited physical strength and are not suitable for many applications. Other approaches for modifying the surfaces of hydrophobic polymeric materials or other biomaterials to achieve a more desirable surface composition for biomedical applications include adsorption of block copolymers, chemical grafting of polymers to the surface, and plasma deposition of an overlying film. Each of these methods suffers various disadvantages. For example, adsorbed block copolymers can be rearranged actively by cells, grafted polymers are difficult to apply at high density on a surface, and plasma deposition results in a gel-like surface structure poorly suited for controlled cell signaling. None of these methods provides a means for modifying the surface of complex three-dimensional structures such as fibrous or sponge-like tissue scaffolds, or for creating clustered ligand distributions of variable concentration and spacing on biomaterial surfaces.

It would be advantageous to provide polymer materials and processing methods that overcome the disadvantages of other biomaterials surface modification approaches. It is therefore an object of the present invention to provide polymer materials that elicit controlled cell-surface interactions by inhibiting protein adsorption, and, where appropriate, presenting controlled concentrations and spatial distributions of cell-signaling ligands on biomaterial surfaces. It is further an object of the present invention to provide processing methods by which such polymers can be placed at a biomaterial surface. It is further the object of the present invention to provide polymeric materials which can be used to create discrete nanometer- to micrometer-sized domains on a biomaterial surface that present two or more different types of ligands for regulating cellular response.

SUMMARY OF THE INVENTION

Comb-type copolymers that elicit controlled cellular response, methods by which such polymers can be localized at a surface, and methods of using such polymers for modifying the surfaces of biomedical devices are disclosed.

The polymers include a hydrophobic, water-insoluble backbone and low molecular weight, hydrophilic, non-cell binding side chains. As defined herein, non-cell binding refers to materials which exhibit no observable cell attachment after standard cell culturing assays in serum containing media for 24 hours. The molecular weight of the hydrophilic side chains is preferably above 200 Daltons and below 2000 Daltons. The backbone can be biodegradable or non-biodegradable, depending on the intended application. Biodegradable backbones are preferred for most tissue engineering, drug delivery and wound healing device applications, while non-biodegradable backbones are desirable for permanent implant, biofiltration, and cell culture plate applications. A portion of the non-cell binding side chains can be end-capped with cell-signaling ligands to control the degree of cell adhesion, or other cell response, elicited by the polymer surface. In the preferred embodiment, the overall comb copolymer should have a molecular weight sufficiently high as to confer good mechanical properties to the polymer in the melt state through chain entanglements. That is, its molecular weight should be above the entanglement molecular weight, as defined by one of ordinary skill in the art. The overall molecular weight of the comb copolymer should thus be above about 10,000 Daltons, more preferably above 20,000 Daltons, and more preferably still above 30,000 Daltons.

The density of the hydrophilic side chains along the backbone of the copolymers depends on the length of the side chains and the water-solubility characteristics of the final polymer. The total percentage by weight of the hydrophilic side chains is between 20 and 60 percent of the total copolymer composition, preferably around 40 percent by weight. For combs incorporating hydrophilic side chains with a molecular weight of about 350 Daltons, the mole percent of segments of the backbone carrying hydrophilic side chains can be as high as 30 percent. For hydrophilic side chains with a molecular weight of about 2000 Daltons, the mole percent of segments of the backbone carrying hydrophobic side chains can be as low as 2 percent. In the preferred embodiment, the overall comb copolymer is not water-soluble. As defined herein, the term water-soluble refers to materials having a solubility in aqueous solutions of greater than 1 gram per liter. When in contact with aqueous solutions, the hydrophilic side chains swell and form a hydrated layer which repels proteins and hence resists cellular adhesion.

The non-cell binding side chains of the comb copolymer can be end-capped with cell-signaling chemical ligands in order to elicit controlled cell responses. Ligands such as adhesion peptides or growth factors can be covalently or ionically attached to the ends of the side chains using known chemistries to provide specific chemical signals to cells. A defined fraction of ligand-bearing side chains can be obtained by using appropriate stoichiometric control during the coupling of the ligands to the polymers, by protecting the end-groups on those side chains which are not to be end-capped with ligands, or by combinations of these approaches. For applications where it is desirable to cluster ligands on the length scale of nanometers or tens of nanometers on a biomaterial surface, more than one ligand (on average) can be covalently attached to a single comb copolymer chain. In applications where it is desirable to incorporate two or more types of ligands in a single cluster on a biomaterial surface on the size scale of nanometers to tens of nanometers, one or more of each of the ligand types (for example, an adhesion peptide and growth factor) can be attached to a single comb copolymer chain through its side chains using known chemistries.

When adhesion peptides are coupled to the comb copolymer side chains, cells attach and spread readily on the comb copolymer surface. The amount of cell spreading and proliferation on the surface therefore can be controlled by mixing adhesion peptide-bearing comb copolymers with non-cell binding comb copolymers, for example, so that less than 20% of the combs bear an adhesion peptide. Similarly, the spatial distribution of ligand clusters on the biomaterial surface can be controlled by mixing non-cell binding comb copolymers with comb copolymers in which each chain on average has more than one ligand attached to its side chains. In this case, the size of the ligand clusters (i.e., the spatial area in which the ligands are localized) is dictated by the characteristic size of the ligand-bearing comb copolymer, and can be approximated from the comb copolymer's radius of gyration, $R_G$, which can be calculated or experimentally determined by one of ordinary skill in the art. The comb copolymer radius of gyration can range typically between nanometers and several tens of nanometers, depending on total molecular weight, length of side chains, and environment surrounding the polymer chain, for example, other polymer chains or water molecules (P. G. deGennes, *Scaling Concepts in Polymer Physics*, Cornell University Press 1979). Thus the size of the ligand clusters, as well as the number and type of ligands per cluster, can be controlled by the synthesis conditions of the ligand-bearing, comb copolymers. For example, a comb copolymer with $R_G=4$ nm would have an area per cluster of $\pi R_G^2$ or approximately 50 nm$^2$. The number of clusters on the surface per unit surface area (on average) can be controlled by the ratio of ligand-bearing to non-cell binding combs at the surface. To achieve a surface separation distance between ligand clusters of d, where $d>2R_G$, the concentration of ligand-bearing combs should be approximately $\phi=V_{chain}/(2R_G d^2)$, where $V_{chain}$ is the volume occupied by a single comb copolymer chain. For example, to achieve a cluster-to-cluster distance of 20 nm with a comb copolymer which has $R_G=4$ nm and $V_{chain}=48$ nm$^3$, the estimated fraction of ligand-bearing combs required is 1.5 vol %. A cluster-to-cluster distance of 10 nm would require 6 vol % of the ligand-bearing comb.

Numerous methods can be used to apply the comb copolymers, or their mixtures, to various biomaterial surfaces. These methods include dip coating, spray coating, brush coating, roll coating, or spin casting a film onto the substrate, typically followed by mild heating to promote adhesion to the surface. Solid free form processes such as three dimensional printing techniques (3DP), or freeze drying methods could be used to create complex three-dimensional structures, including porous structures. In all of these processing approaches a suitable crosslinking agent might be incorporated to enhance the mechanical rigidity of the film or device.

In applications where it is desirable to use only small amounts of copolymer to modify the surface of a second, hydrophobic or non-cell regulating polymer, the comb copolymers can be added in small quantities to the second polymer and processed to achieve segregation of the comb copolymer to the surface. In preferred embodiments, the comb copolymer would comprise less than 10 wt % of the polymer mixture. Processing steps to achieve segregation include heating the mixture under a vacuum, in air, water, water vapor, $CO_2$ or other environment which favors the comb component at the surface, at temperatures sufficiently above the glass transitions of the polymer components to provide mobility for achieving surface segregation. In the case where the second polymer component is a semicrystalline polymer, the annealing temperature should be above the glass transition but below the melting point of the polymer, to ensure that the desired shape of the device is retained. In preferred embodiments, surface segregation is achieved during a standard processing step in the manufacture of a biomedical device, such as during an extraction, autoclaving or sterilization process. In other embodiments, segregation is accomplished in an additional annealing step in a controlled environment (water, etc), after device fabrication. Such processing steps create a surface layer approximately $2R_G$ in thickness that contains almost exclusively the comb copolymer. The observable surface properties of such annealed mixtures are substantially identical to those of the pure comb copolymers. In preferred embodiments, the comb copolymer is miscible with the second polymer to avoid phase separation in the bulk device, which might lead to poor mechanical or optical properties.

In other cases, the localization of the comb polymer to the surface of a device primarily comprised of a second, hydrophobic or non-cell regulating polymer can be accomplished during other steps of device manufacture. For example, precise placement of the comb copolymer at the surface of a device made from a second polymer can be accomplished by 3DP methods. Likewise, differences in viscosity between the comb copolymer and a second polymer when blended together can be exploited to locate the comb to the surface during melt extrusion of fibers, films or other devices. Porous or nonporous membranes, films, fibers or hollow fibers in which the comb copolymer resides at the surfaces can be prepared by phase inversion casting. In this method, a solution of the comb copolymer, the second polymer, and a mutual solvent is cast into an aqueous-based coagulation bath to form the device. During the casting process, favorable interactions between the comb and the coagulation bath medium induce segregation of the comb copolymer to exterior surfaces of the film, fiber, or membrane. Cell-regulating microporous biodegradable membranes useful as temporary barrier devices in wound-healing applications can be prepared in this fashion. Cell-regulating biodegradable sutures can similarly be prepared by spinning fibers from solution into an aqueous-based coagulation bath. Such surface-modified fibers can also be prepared from biodegradable or nonbiodegradable materials and fashioned into nonwoven fabric articles for biomedical applications including cell-regulating temporary barrier devices and biofiltration devices. Hollow nanoporous fibers can be prepared which have cell-regulating interior surfaces. By encapsulating cells in a portion of such a fiber, a long-term drug delivery implant could be prepared which secretes desirable products of cells in quantities regulated wholly or in part by tethered signals on the fiber inner surface. Cell-regulating biodegradable microporous scaffolds with a surface excess of comb copolymers can be prepared by freeze-drying methods by choosing a sublimating solvent which has preferential affinity to the comb copolymer component as compared to the second polymer component which forms the bulk of the device.

In all cases described above where comb copolymers are used in conjunction with a second polymer to prepare a device, the comb copolymers can be non-cell binding combs, ligand-bearing combs, or a mixture of these to achieve a desired cell response as previously described.

A further method by which the comb copolymers can be used for controlling cell response in biomedical applications is through the preparation of polymer latexes that incorporate the comb copolymers on the latex particle surfaces. Such latexes are prepared by dispersion or emulsion polymerization methods in a water-containing medium, using the comb copolymers as a stabilizing agent. The polymerization is achieved by dissolving or mixing the desired monomer, comb stabilizer and initiator in a water-containing medium. The polymer is initiated, for example, by applying heat to the solvent. The dispersion medium is a good solvent for the comb copolymer but a poor solvent for the growing polymer. The hydrophobic comb backbone is chosen to be compatible with the polymer being synthesized, and thus anchors to the surface of the growing polymer particles, while the hydrophilic side chains stabilize the particles against flocculation. Upon completion of the latex synthesis, the resulting latex particles are in the range of 0.1 to 10 $\mu$m in size, typically dispersed at 20–70% polymer solids by weight in the dispersion medium. These systems can be employed in a variety of ways to control cell response through the comb copolymers that remain anchored to the particle surfaces.

Films or coatings can be prepared from the latex dispersions by usual methods such as dipping, brushing, rolling or casting the latex onto any surface. For coatings applied to permanent implants to control cell response, nonbiodegradable latex particles are preferred, such as acrylics. Opaque coatings may be prepared that elicit controlled cell response by employing any of the standard coating methods used to form latex films by those skilled in the art, such as those just mentioned. Alternatively, by heat-treating films at a temperature well above the glass transition of the polymer particles, the particles will coalesce into a smooth, transparent film in which the comb copolymers reside at the surface. The comb copolymers remain localized at the surface upon coalescence due either to an energetic tendency to remain at the surface, or because there is insufficient mobility for comb diffusion into the bulk of the coalesced latex film, for example, if the film is cooled below its glass transition shortly after coalescence. The latex films exhibit surface properties akin to the comb copolymers themselves, but have the advantages that only small quantities of the comb copolymer are used (typically below 1 wt % of the total latex), coatings can be easily applied from water-based suspensions, and the film-forming properties can be tailored to adhere to the substrate by judicious choice of the film-forming polymer. For example, an acrylic latex stabilized by non-cell binding comb copolymers could be used to prepare transparent acrylic coatings on acrylic intraocular lenses in order to render them resistant to cell attachment, and hence less subject to clouding over time. Acrylic latexes could also be used in applications where controlled cell response is desired at the surface of permanent metal, glass or ceramic implants or other devices, including cell culture apparatus, since a high degree of adhesion is often found between oxide surfaces and acrylic polymers. For polystyrene cell culture plates or other apparatus, a cell-regulating PS latex could be used to prepare a transparent, cell-regulating coating in the manner described above.

In all cases described above where latexes are stabilized by comb copolymers, the comb copolymers might be non-cell binding combs, ligand-bearing combs, or a mixture of these to achieve a desired cell response as previously described above. Alternatively, mixed latex dispersions can be used to prepare films which contain clustered ligand regions on a surface of sizes from 0.1 to 10 micrometers. This can be achieved by mixing together dispersions of latex particles coated with non-cell binding combs and those coated with ligand-bearing combs and creating films of these mixed dispersions as described above. The size of the ligand clusters is approximately the diameter of the latex particles coated with ligand-bearing combs, while the number of clusters on the surface per unit surface area can be controlled by the ratio of ligand-bearing to non-cell binding latex particles in the mixed dispersion.

For applications where a biodegradable film is preferred, biodegradable latexes can be prepared using comb stabilizers with biodegradable backbones. Such biodegradable latexes could also be employed as drug delivery vehicles as described below.

DETAILED DESCRIPTION OF THE INVENTION

Comb-type copolymers that elicit regulated cellular response, methods by which such polymers can be localized at a surface, and methods of using such polymers for modifying the surfaces of biomedical devices are disclosed. These polymers are characterized by properties that are a function of the type and ratio of hydrophilic side chains to hydrophobic backbone polymers, type and number of tethered cell-signaling ligands, molecular weight, and processing conditions.

I. Polymer Composition

A. Polymer Architecture

The polymers are comb-type copolymers, with a backbone formed of a hydrophobic, water-insoluble polymer and side chains formed of short, hydrophilic non-cell binding polymers, having a molecular weight of between 200 and 2000 Daltons. The hydrophobic backbone can be biodegradable or non-biodegradable, depending on the desired application. The overall comb copolymer should have a molecular weight sufficiently high in the melt state as to confer good mechanical properties to the polymer through chain entanglement, that is, its molecular weight should be above the entanglement molecular weight, as defined by one of ordinary skill in the art. The overall molecular weight of the comb copolymer should thus be above about 10,000 Daltons, more preferably above 20,000 Daltons, and more preferably still above 30,000 Daltons. The comb copolymers can be prepared by copolymerizing a hydrophilic macromonomer which contains a polymerizable chain end with a second hydrophobic monomer. Alternatively, a hydrophobic monomer can be copolymerized with a second monomer that includes suitable reactive groups through which the hydrophilic side chains can be grafted to the backbone. Alternatively, a hydrophobic monomer with a suitable reactive side group can be polymerized and a fraction of those reactive side groups can be modified by grafting hydrophilic side chains. A defined percentage of the non-cell binding side chains can be end-capped with a suitable ligand to elicit a specific cellular response.

B. Hydrophobic Polymer Backbones

1. Biodegradable Hydrophobic Polymers

Hydrophobic polymers used to impart biodegradable properties to the backbones of the comb copolymers are preferably hydrolyzable under in vivo conditions. Suitable biodegradable polymeric units include hydroxy acids or other biologically degradable polymers that yield degradation products that are non-toxic or present as normal metabolites in the body. These include poly(amino acids), poly(anhydrides), poly(orthoesters), and poly (phosphoesters). Polylactones such as poly(epsilon-caprolactone), poly(delta-valerolactone), poly(gamma-butyrolactone)and poly (beta-hydroxybutyrate), for example, are also useful. Preferred poly(hydroxy acid)s are poly(glycolic acid), poly(DL-lactic acid) and poly(L-lactic acid), or copolymers of poly(glycolic acid) and poly(lactic acid). In general, these materials degrade in vivo by both non-enzymatic and enzymatic hydrolysis, and by surface or bulk erosion.

Biodegradable regions can be constructed from monomers, oligomers or polymers using linkages susceptible to biodegradation, such as ester, peptide, anhydride, orthoester, and phosphoester bonds.

2. Non-Biodegradable Hydrophobic Polymers

Representative non-biodegradable, hydrophobic polymers that could be incorporated into the backbone of the comb copolymers include polyalkylenes such as polyethylene and polypropylene, polychloroprene, polyvinyl ethers, polyvinyl esters such as poly(vinyl acetate), polyvinyl halides such as poly(vinyl chloride), polysiloxanes, polystyrene, polyurethanes and copolymers thereof, polyacrylates, such as poly(methyl (meth)acrylate), poly (ethyl (meth)acrylate), poly(butyl(meth)acrylate), poly (isobutyl (meth)acrylate), poly(hexyl(meth)acrylate), poly (isodecyl (meth)acrylate), poly(lauryl (meth)acrylate), poly (phenyl (meth)acrylate), poly(methyl acrylate), poly (isopropyl acrylate), poly(isobutyl acrylate), and poly (octadecyl acrylate) (jointly referred to herein as "polyacrylates"), and copolymers and mixtures thereof. The polymers include useful derivatives, including polymers having substitutions, additions of chemical groups, for example, alkyl groups, alkylene groups, hydroxylations, oxidations, and other modifications routinely made by those skilled in the art.

Preferred non-biodegradable polymers include ethylene vinyl acetate, polyacrylates, poly(chloroprene), and copolymers and mixtures thereof

C. Non-Cell Binding Hydrophilic Side Chains

The non-cell binding side chains are preferably water-soluble when not attached to the backbone, and, more preferably, are non-ionic. Suitable polymeric blocks include those prepared from poly(ethylene glycol), poly(ethylene oxide), partially or fully hydrolyzed poly(vinyl alcohol), poly(vinylpyrrolidone), and dextran. Preferably, the side chains are made from poly(ethylene glycol), poly(ethylene oxide), or poly(acrylic acids).

The hydrophilic side chains may be intrinsically biodegradable or may be poorly biodegradable or effectively non-biodegradable in the body. In the latter two cases, the side chains should be of sufficiently low molecular weight to allow excretion. The preferred molecular weight range is below about 2000 Daltons, more preferably below 1000 Daltons, and most preferably, below about 500 Daltons. When the polymer is polyethylene glycol, it is preferred that the number of ethylene oxide monomeric units is between about 4 and 20.

When double-bond containing monomers are used to prepare the polymer backbone, a preferred method for incorporating the hydrophilic side chains is to use a hydrophilic macromonomer with a reactive double bond at one end which can be randomly incorporated during free radical or other addition polymerization. An example of such a macromonomer is PEG-methacrylate. The density of the non-cell binding, hydrophilic side chains along the polymer backbone is controlled by controlling the relative amounts of the PEG-methacrylate or other suitable macromonomeric unit used.

In those embodiments in which the side groups are end capped with cell-signaling ligands, appropriate functional groups, such as —$NH_2$, —OH, or COOH are included on the ends of the macromonomers.

D. Monomers with Reactive Functional Groups

In many of the embodiments described herein, the monomers used to form the polymer backbone include only two reactive groups, both of which are reacted in order to form the polymer. For example, lactic acid includes two reactive groups, a hydroxy group and a carboxy group. —OH is the preferred reactive group. Although the ends of a polylactic acid polymer include a hydroxy group and a carboxy group, there are no reactive groups along the backbone in the final polymer chain that can be used to form a comb copolymer.

Monomers which contain one or more additional reactive groups need to be incorporated into the polymer backbone, preferably in a random fashion, in order to form the comb-type copolymers when monomers that do not include these reactive groups are used to prepare the polymer backbone. Examples of these types of monomers are well known to those of skill in the art.

The requirements for a suitable reactive monomer are that it can be incorporated in the growing polymer chain by participating in the same types of chemical reactions as the growing polymer chain. For example, when lactide is being polymerized using a Lewis acid catalyst, a depsipeptide (cyclic dimer of an amino acid) can be prepared from lysine, in which the epsilon amine group is protected, for example, with a t-boc protecting group. The lysine is incorporated into the polymer, and the protecting group can be removed. The resulting amine groups are reactive with hydrophilic polymers which include leaving groups such as tosylates, tresylates, mesylates, triflates and other leaving groups well known to those of skill in the art.

Alternatively, the reactive monomer can include a leaving group that can be displaced with a nucleophilic group on a hydrophilic polymer. For example, epichlorohydrin can be used during the polymerization step. The monomer is incorporated into the polymer backbone, and the chloride group is present on the backbone for subsequent reaction with nucleophiles. An example of a suitable hydrophilic polymer containing a nucleophilic group is a PEG with a terminal amine group. PEG-$NH_2$ can react with the chloride groups on the polymer backbone to provide a desired density of PEG-ylation on the polymer backbone. Using the chemistry described herein, along with the general knowledge of those of skill in the art, one can prepare polymer backbones which include suitable leaving groups or nucleophiles for subsequent coupling reactions with suitably functionalized hydrophilic polymers.

E. Ligands for Controlling Cell Response

A number of molecules are known to promote cell adhesion. These can be amino acids, peptides or glycoproteins. Exemplary cell-binding ligands include peptides possessing an Arginine-Glycine-Aspartic acid (RGD) amino acid sequence or a Tyrosine-Isoleucine-Serine-Arginine-Glycine (YISRG). The RGD sequence, present in proteins such as fibronectin, has been shown to be active in promoting cell adhesion and growth (Massia, S. P. and Hubbell, J. A., *J Cell. Biol.*, 114:1089 (1991)). Incorporation of RGD sequences at the ends of the copolymer side chains thus can enhance cell adhesion and growth. This is particularly useful when a substrate is not adhesive, for example, a polyester to which cells such as hepatocytes show poor adhesion, which is then modified with the comb copolymer to promote cellular adhesion in a controlled manner.

Biologically active molecules may also be incorporated into the copolymer to promote the adhesion and growth of a particular cell type in vivo. Many growth factors are known and can be obtained from commercial sources such as Sigma Chemical Co, St. Louis, Mo., for example, growth factors including epidermal growth factor, vascular endothelial growth factor, fibroblast growth factor, etc.

F. Relative Ratios of Comb Components

1. Ratio of Hydrophilic to Hydrophobic Units

The density of the hydrophilic side chains along the polymer backbone depends in part on the molecular weight of the side chains. The total percent of the hydrophilic units to the hydrophobic units in the comb copolymers is between 20 and 60 percent by weight, preferably around 40 percent by weight. For hydrophilic side chains with a molecular weight of about 350, the mole percent of backbone segments carrying hydrophilic side chains can be as high as about 30 percent. For hydrophilic side chains with a molecular weight of about 2000, the mole percent can be as low as about 2 percent.

The relevant consideration when determining an appropriate ratio of hydrophilic to hydrophobic units in the comb copolymers is that the overall polymer, when the hydrophilic side chains are not end-capped with cell-signaling ligands, has the defined non-cell binding properties and preferably is not water-soluble. A relatively high density of very short (MW 500 or less) hydrophilic side chains can provide the same degree of resistance to cellular adhesion as a lower density of higher molecular weight (for example, a MW between 1500 and 2000) side chains. Those of skill in the art can adjust the molecular weight and density of the polymers taking these factors into consideration.

2. Density of Tethered Ligands

The non-cell binding side chains of the comb copolymers can be end-capped with cell-signaling chemical ligands in order to elicit specific cell responses. Ligands such as adhesion peptides or growth factors can be covalently or ionically attached to the ends of the side chains using known chemistries to provide specific chemical signals to cells. A defined fraction of ligand-bearing side chains can be obtained by using appropriate stoichiometric control during the coupling of the ligands to the ends of the side chains, by protecting the end-groups on those side chains which are not to be end-capped with ligands, or by combinations of these approaches. For applications where it is desirable to cluster ligands on the length scale of nanometers or tens of nanometers on a biomaterial surface, more than one ligand (on average) can be attached to each comb copolymer chain. In applications where it is desirable to incorporate two or more types of ligands in a single cluster on a biomaterial surface on the size scale of nanometers to tens of nanometers, one or more of each of the ligand types (for example, an adhesion peptide and growth factor) can be attached to each comb copolymer chain (on average) using known chemistries. Presentation of the ligand (or ligands) at the surface can thus be tailored in terms of overall surface density by exploiting the multi-branch nature of the comb molecule, in terms of local density, by the number of ligands attached to the same comb. The ability of the polymers to control cellular adhesion or other cell function can be adjusted by controlling the density of the cell-signaling ligands presented at the surface.

II. Polymer Mixtures

A. Mixtures of Comb Copolymers

When adhesion peptides are coupled to the comb copolymer side chains, cells attach and spread readily on the comb copolymer surface. The amount of cell spreading and proliferation on the surface therefore can be controlled by mixing adhesion peptide-bearing comb copolymers with non-cell binding comb copolymers, for example, so that less than 20%, more typically less than 2%, of the combs bear an adhesion peptide. Similarly, the spatial distribution of ligand clusters on the biomaterial surface can be controlled by mixing non-cell binding comb copolymers with comb copolymers in which each chain on average has more than one ligand attached to its side chains.

The size of the ligand clusters (i.e., the spatial area in which the ligands are localized) is dictated by the characteristic size of the ligand-bearing comb copolymer, and can be approximated from the comb copolymer's radius of gyration, $R_G$, which can be calculated or experimentally determined by one of ordinary skill in the art. The comb copolymer radius of gyration can range typically between nanometers and several tens of nanometers, depending on total molecular weight, length of side chains, and environment surrounding the polymer chain, for example, other polymer chains or water molecules. Thus the size of the ligand clusters, as well as the number and type of ligands per cluster, can be controlled by the synthesis conditions of the ligand-bearing comb copolymers. For example, a comb copolymer of $R_G$ would have an area per cluster of $\pi R_G^2$. The number of clusters on the surface per unit surface area (on average) can be controlled by the ratio of ligand-bearing to non-cell binding combs at the surface. To achieve a surface separation distance between ligand clusters of d, where $d>2R_G$, the concentration of ligand-bearing combs should be approximately $\phi=V_{chain}/(2R_G d^2)$, where $V_{chain}$ is the volume occupied by a single comb copolymer chain.

B. Mixtures of Comb Copolymers and Other Polymers

The copolymers described herein can be blended with other polymers that do not elicit controlled cell responses. In applications where it is desirable to use the comb copolymer to modify the surface of a second, hydrophobic or non-cell regulating polymer, the comb copolymer can be added in small quantities to the second polymer and processed to achieve comb segregation to the surface. Blends of the comb copolymers with other polymers include those containing between 1 and 99% by weight of the comb copolymers, preferably less than 20 wt % of the comb copolymers, and more preferably less than 10 wt % of the comb copolymers. Processing steps to achieve comb surface segregation include heating the mixture under vacuum, in air, water, water vapor, supercritical $CO_2$ or other environment that favors the comb component at the surface, at temperatures sufficiently above the glass transitions of the polymer components (the matrix polymer and the comb copolymer additive) to provide mobility for achieving surface segregation. In the case where the second polymer component is a semicrystalline polymer, the annealing temperature should be above the glass transition but below the melting point of the polymer, to ensure that the desired shape of the device is retained.

In preferred embodiments, surface segregation is achieved during a standard processing step in the manufacture of a biomedical device, such as during an extraction, autoclaving or sterilization process. In other embodiments, segregation is accomplished in an additional annealing step in a controlled environment (water, etc), after device fabrication. Such processing steps create a surface layer approximately 2RG in thickness that contains almost exclusively the comb copolymer. The observable surface properties of such annealed mixtures are substantially identical to those of the pure comb copolymers. In preferred embodiments, the comb copolymer is miscible with the second polymer to avoid phase separation in the bulk device, which might lead to poor mechanical or optical properties.

In other cases, the localization of the comb polymer to the surface of a device primarily comprised of a second, hydrophobic or non-cell regulating polymer can be accomplished during other steps of device manufacture. For example, precise placement of the comb copolymer at the surface of a device made from a second polymer can be accomplished by 3DP methods.

Likewise, differences in viscosity between the comb copolymer and a second polymer when blended together can be exploited to locate the comb to the surface during melt extrusion of fibers, films or other devices. Porous or nonporous membranes, films, fibers or hollow fibers in which the comb copolymer resides at the surfaces can be prepared by phase inversion casting. In this method, a solution of the comb copolymer, the second polymer, and a mutual solvent is cast into an aqueous-based coagulation bath to form the device. During the casting process, favorable interactions between the comb and the coagulation bath medium induce segregation of the comb copolymer to exterior surfaces of the film, fiber, or membrane. Cell-regulating microporous biodegradable membranes useful as temporary barrier devices in wound-healing applications can be prepared in this fashion. Cell-regulating biodegradable sutures can similarly be prepared by spinning fibers from solution into an aqueous-based coagulation bath. Such surface-modified fibers can also be prepared from biodegradable or nonbiodegradable materials and fashioned into nonwoven fabric articles for biomedical applications including cell-regulating temporary barrier devices and biofiltration devices. Hollow nanoporous fibers can be prepared which have cell-regulating interior surfaces. By encapsulating cells in a portion of such a fiber, a long-term drug delivery implant could be prepared which secretes desirable products of cells in quantities regulated wholly or in part by tethered signals on the fiber inner surface. Cell-regulating biodegradable microporous scaffolds with a surface excess of comb copolymers can be prepared by freeze-drying methods by choosing a sublimating solvent which has preferential affinity to the comb copolymer component as compared to the second polymer component which forms the bulk of the device.

In all cases described above where comb copolymers are used in conjunction with a second polymer to prepare a device, the comb copolymers can be non-cell binding combs, ligand-bearing combs, or a mixture of these to achieve a desired cell response as previously described. The observable surface properties of the device are substantially identical to those of the comb copolymer or comb copolymer mixture itself.

III. Latexes Prepared with Comb Copolymers

A. Latex Synthesis

A further method by which the comb copolymers can be used for controlling cell response in biomedical applications is through the preparation of polymer latexes that incorporate the comb copolymers on the latex particle surfaces. Such latexes can be prepared by dispersion or emulsion polymerization methods in a water-containing medium, using the comb copolymers as a stabilizing agent. The polymerization is achieved by dissolving the desired monomer, comb stabilizer and initiator in a water-containing medium. The polymer is initiated, for example, by applying heat to the solvent. The dispersion medium is a good solvent for the comb copolymer but a poor solvent for the growing polymer. The hydrophobic comb backbone is chosen to be compatible with the polymer being synthesized, and thus anchors to the surface of the growing polymer particles, while the hydrophilic side chains stabilize the particles against flocculation. Upon completion of the latex synthesis, the resulting latex particles are in the range of 0.1 to 10 $\mu$m in size, typically dispersed at 20–70% polymer solids by weight in the dispersion medium. These systems can be employed in a variety of ways to control cell response through the comb copolymers that remain anchored to the particle surfaces.

Polymers which might be synthesized as latex particles for non-biodegradable applications include polyvinyl ethers, polyvinyl esters such as poly(vinyl acetate), polyvinyl halides such as poly(vinyl chloride), polystyrene, and polyacrylates, such as poly(methyl (meth)acrylate), poly (ethyl (meth)acrylate), poly(butyl(meth)acrylate), poly (isobutyl (meth)acrylate), poly(hexyl(meth)acrylate), poly (isodecyl (meth)acrylate), poly(lauryl (meth)acrylate), poly (phenyl (meth))acrylate), poly(methyl acrylate), poly (isopropyl acrylate), poly(isobutyl acrylate), and poly (octadecyl acrylate), and copolymers and mixtures thereof, as well as useful derivatives of these polymers, including polymers having substitutions, additions of chemical groups, for example, alkyl groups, alkylene groups, hydroxylations, oxidations, and other modifications routinely made by those skilled in the art.

Polymers which might be synthesized as latex particles for biodegradable applications include poly(amino acids), poly(anhydrides), poly(orthoesters), and poly (phosphoesters), polylactones such as poly(epsilon-caprolactone), poly(delta-valerolactone), poly(gamma-butyrolactone)and poly (beta-hydroxybutyrate), and poly (hydroxy acid)s such as poly(glycolic acid), poly(DL-lactic acid) and poly(L-lactic acid), or copolymers of poly(glycolic acid and poly(lactic acid).

B. Latex Films

Films or coatings can be prepared from the latex dispersions by usual methods such as dipping, brushing, rolling or casting the latex onto any surface. For coatings applied to permanent implants to control cell response, non-biodegradable latex particles prepared with non-biodegradable comb stabilizers are preferred. For applications where a biodegradable film is preferred, biodegradable latexes can be prepared using comb stabilizers with biodegradable backbones. Opaque coatings may be prepared that elicit controlled cell response by employing any of the standard coating methods used to form latex films, such as those just mentioned. Alternatively, by heat-treating films at a temperature well above the glass transition of the polymer particles, the particles will coalesce into a smooth, transparent film in which the comb copolymers reside at the surface. The comb copolymers remain localized at the surface upon coalescence due either to an energetic tendency to remain at the surface, or because there is insufficient mobility for comb diffusion into the bulk of the coalesced latex film, for example, if the film is cooled below its glass transition shortly after coalescence.

The latex films exhibit surface properties of the comb copolymers themselves, but have the advantages that only small quantities of the comb copolymer are required (typically below 1 wt % of the total latex), coatings can be easily applied from water-based suspensions, and the film-forming properties can be tailored to adhere to the substrate by judicious choice of the film-forming polymer. For example, an acrylic latex stabilized by non-cell binding comb copolymers could be used to prepare transparent acrylic coatings on acrylic intraocular lenses in order to render them resistant to cell attachment, and hence less subject to clouding over time. Acrylic latexes could also be used in applications where controlled cell response is desired at the surface of permanent metal, glass or ceramic implants or other devices, including cell culture apparatus, since a high degree of adhesion is often found between oxide surfaces and acrylic polymers. For polystyrene cell culture plates or other apparatus, a cell-regulating PS latex could be used to prepare a transparent, cell-regulating coating in the manner described above.

In all cases described above where latexes are stabilized by comb copolymers, the comb copolymers might be non-cell binding combs, ligand-bearing combs, or a mixture of these to achieve a desired cell response as previously described above. Alternatively, mixed latex dispersions can be used to prepare films that contain clustered ligand regions on a surface of sizes from 0.1 to 10 micrometers. This can be achieved by mixing together dispersions of latex particles coated with non-cell binding combs and those coated with ligand-bearing combs and creating films of these mixed dispersions as described above. The size of the ligand clusters is approximately the diameter of the latex particles coated with ligand-bearing combs, while the number of clusters on the surface per unit surface area can be controlled by the ratio of ligand-bearing to non-cell binding latex particles in the mixed dispersion.

IV. Polymer Preparation

Methods for preparing hydrophobic polymers including reactive monomeric units are known. Typical reactions are ring opening polymerization (for monomers such as lactide, glycolide, and other cyclic monomeric units), free radical polymerization (for double bond-containing monomeric units such as methyl methacrylate), and anionic or other addition polymerizations.

The monomers used to prepare the hydrophobic polymer backbone, for example, lactide, glycolide, caprolactone, and trimethylene carbonate, can be reacted with various polymerization initiators, for example, alcohols such as ethylene glycol and ethanol, water, and amines, in the presence of a suitable catalyst such as a Lewis acid, as described, for example, in Kricheldorf, H. R. in *Models of Biopolymers by Ring-Opening Polymerization,* Penczek, S., Ed., CRC Press, Boca Raton, 1990, Chapter 1; Kricheldorf, H. R. α-*Aminoacid-N-Carboxy-Anhydrides and Related Heterocycles,* Springer-Verlag, Berlin, 1987; and Imanishi, Y. in *Ring-Opening Polymerization,* Ivin, K. J. and Saegusa, T., Eds., Elsevier, London, 1984, Volume 2, Chapter 8.

The cell-binding polymer side chains grafted onto the polymer backbone are preferably hydrophilic polymers, such as polyethylene glycol, polyethylene oxide, polyacrylic acid, dextran and mixtures thereof, which can be modified to include reactive functional groups such as amino, carboxylic acid, halo, sulfide, guanidino, imidazole and hydroxyl groups. These groups can react with various reactive groups on the polymer backbone in routine nucleophilic displacement reactions to graft the hydrophilic polymers to the backbone. The side chain polymers can be end-capped with cell binding ligands through standard covalent or ionic coupling reactions.

V. Surface Coatings and Devices Incorporating Comb Copolymers

Numerous methods can be used to apply the comb copolymers, comb copolymer mixtures, or mixtures of comb copolymers and other polymers to surfaces. These methods include dip coating, spray coating, brush coating, roll coating, or spin casting a film onto the substrate followed by mild heating to promote adhesion to the surface. Solid free form processes such as 3DP, or freeze drying methods could be used to create complex three-dimensional structures, including porous structures. In all of these processing approaches a suitable crosslinking agent might be incorporated to enhance the mechanical rigidity of the coating or device.

In applications where mixtures of comb copolymers with other polymers are desirable, processing steps to achieve comb surface segregation include heating the mixture under vacuum, in air, water, water vapor, supercritical $CO_2$ or other environment that favors the comb component at the surface, at temperatures sufficiently above the glass transitions of the polymers to provide the combs with the necessary mobility. In the case where the second polymer component is a semicrystalline polymer, the annealing temperature should be above the glass transition but below the melting point of the polymer, to ensure that the desired shape of the device is retained.

Surface segregation could be achieved preferably during a standard processing step in the manufacture of a biomedical device, such as during an extraction, autoclaving or sterilization process, or could be accomplished in a separate annealing step after the device has been manufactured. This type of processing creates a surface layer on the device that contains almost exclusively the comb copolymer. In other cases, the localization of the comb polymer to the surface of a device primarily comprised of a second polymer can be accomplished during other steps of device manufacture. For example, differences in viscosity between the comb copolymer and a second polymer when blended together can be exploited to locate the comb to the surface during melt extrusion of fibers, films or other devices. Porous or nonporous membranes, films, fibers or hollow fibers in which the comb copolymer resides at the surfaces can be prepared by phase inversion casting. In this method, a solution of the comb copolymer, the second polymer, and a mutual solvent is cast into an aqueous-based coagulation bath to form the device. During the casting process, favorable interactions between the comb and the coagulation bath medium induce segregation of the comb copolymer to exterior surfaces of the film, fiber, or membrane. Cell-regulating microporous biodegradable membranes useful as temporary barrier devices in wound-healing applications can be prepared in this fashion. Cell-regulating biodegradable sutures can similarly be prepared by spinning fibers from solution into an aqueous-based coagulation bath. Such surface-modified fibers can also be prepared from biodegradable or nonbiodegradable materials and fashioned into nonwoven fabric articles for biomedical applications including cell-regulating temporary barrier devices and biofiltration devices. Hollow nanoporous fibers can be prepared which have cell-regulating interior surfaces. By encapsulating cells in a portion of such a fiber, a long-term drug delivery implant could be prepared which secretes desirable products of cells in quantities regulated wholly or in part by tethered signals on the fiber inner surface. Cell-regulating biodegradable microporous scaffolds with a surface excess of comb copolymers can be prepared by freeze-drying methods by choosing a sublimating solvent which has preferential affinity to the comb copolymer component as compared to the second polymer component which forms the bulk of the device.

V. Biomedical Applications

The comb-type copolymers described herein may be used in a variety of biomedical applications, such as in scaffolds and supports for cell growth in tissue engineering, coatings for biomedical implants such as intraocular lenses or other permanent implants made from polymeric, metal, glass, or ceramic materials, and coatings for cell culture apparatus such as cell culture plates, pipets, etc.. The comb-type copolymers may be used for modifying the surface properties of sutures, temporary barrier films or fabrics in wound-healing applications, artificial hearts and blood vessels, catheters, filters for blood or other body fluids, and targeted controlled-release drug delivery vehicles and encapsulated cell drug delivery systems. The materials are preferably biodegradable when used for tissue engineering, wound healing, and targeted drug delivery applications, and are preferably non-degradable when used to modify implants, cell culture apparatus, filtration devices, and other devices intended for long term use or implantation.

A. Tissue Engineering

For use in tissue engineering applications, the comb copolymers may be derivatized by the attachment to the ends of the hydrophilic side chains biologically active molecules that promote favorable cell-polymer interactions, such as cell adhesion molecules and growth factors. Matrices suitable for seeding or ingrowth of cells can be formed which incorporate the comb copolymers, or a matrix formed of a material such as stainless steel, collagen, or another polymer can be coated with the comb copolymers. The matrix is then either seeded with cells and implanted, or the matrix implanted for tissue ingrowth to occur. These materials can be tailored to fit the particular needs of a variety of cell types through changes in the type and density of cell adhesion peptides attached to the copolymers. Cell types which can be seeded on the matrices include parenchymal cells such as hepatocytes, uroendothelial cells, skin cells, muscle cells, nerve cells and bone and/or cartilage forming cells. Normal cells, fetal cells or genetically engineered cells can be seeded onto the matrices

B. Drug Delivery and Imaging

The comb copolymers also may be formed into matrices for use as drug delivery systems or for imaging purposes. Biodegradable latexes coated with the comb copolymers be can be used for targeted delivery of a therapeutic, prophylactic or diagnostic agent. Hollow nanoporous fibers can be prepared which have cell-regulating interior surfaces comprised of comb copolymers or comb copolymer mixtures. By encapsulating cells in a portion of such a fiber, a long-term drug delivery implant could be prepared which secretes desirable products of cells in quantities regulated wholly or in part by tethered signals on the fiber inner surface.

For use in drug delivery, a therapeutic or prophylactic agent, such as an amino acid, bioactive peptide or protein, carbohydrate, sugar, or polysaccharide, nucleic acid or polynucleic acid, synthetic organic compound, or metal may be attached to through the end groups of the hydrophilic side chains of the comb copolymer using methods available in the art. The comb copolymers may be modified to increase the level of the incorporated agent. Agents which provide greater stability for the agent to be delivered may be covalently or ionically attached to the copolymer. The comb copolymers may be functionalized with a specific binding moiety, e.g., an antibody, which targets the latex particle for delivery to a particular site within the body. Hydrophilic, hydrophobic, acidic, basic or ionic side chains also may be attached to the copolymers to expand their use as delivery devices for drugs. Matrices of the modified drug-containing comb copolymer may be administered to an animal orally or parenterally to deliver the drug to the animal in vivo at a site in the animal where it is needed.

Diagnostic agents include radioactive materials, fluorescent materials, enzymatic materials, gases, and magnetic materials.

C. Use of the Materials to Provide Cell Repulsive Surfaces

It is often desirable to minimize cell and tissue interactions with biomedical implants, such as intraocular lenses. These interactions are minimized when the surface of an implant is coated with the non-cell binding copolymers. It is preferred that the copolymer be non-degradable in some applications. For example, when intraocular lenses are implanted, they are intended to remain in place for extended periods of time and biodegradability is to be avoided.

A preferred non-biodegradable polymeric material is a copolymer of an alkyl acrylate (i.e., methyl methacrylate) and PEG-methacrylate. A preferred method to place this coating at the surface is through the formation of a latex film.

The present invention will be further understood by references to the following non-limiting examples, in which the following materials and equipment were utilized.

Example 1

Preparation, Processing, and Evaluation of Biodegradable Comb Copolymers and Their Blends
Comb Polymer Synthesis Lactide, epichlorohydrin, poly(ethylene glycol) methyl ether (MPEG, $M_w$~350 g/mole), poly(ethylene glycol) (PEG, $M_w$~400 g/mole), and anhydrous toluene (all from Aldrich Chemical Co.) were used as received. Tetrahydrofuran (Aldrich Chemical Co.) was distilled prior to use. Lactide and epichlorohydrin (Aldrich Chemical Co.) were copolymerized by ring opening polymerization (Shell et al. *J. Polym. Sci., Polym. Chem. Ed.,* 31:1393 (1993)) at 100° C. in toluene with a trioctyl aluminum-water catalyst. The in situ $AlOct_3:0.5H_2O$ catalyst was prepared using a modification of a literature procedure. Briefly, $AlOct_3$ (25 wt % in hexane, Aldrich Chemical Co.) and distilled THF were stirred in a sealed flask under nitrogen and allowed to equilibrate at −68° C. in a dry ice/acetone bath. $H_2O$ was added to the mixture to give a 1:0.5 molar ratio between $AlOct_3$ and water. The mixture was stirred vigorously at −68° C. for 15 minutes, then removed from the dry ice bath and allowed to return to room temperature over 30 minutes. The catalyst solution was then injected into a sealed reaction flask containing lactide, epichlorohydrin, and toluene under nitrogen and allowed to react 16 hours at 100° C. The resulting LA-EO copolymer was purified by repeated precipitation in petroleum ether.

Grafting of MPEG and PEG to the LA-EO copolymer was performed by phase transfer catalysis (Ober, *Makromol. Chem., Macromol. Symp.* 35:36–87(1990)) reacting the terminal hydroxyls of the ethylene glycol chains with the pendant chlorine groups of the backbone copolymer. The LA-EO copolymer was dissolved in methylene chloride. PEG, MPEG, and pH 8 aqueous $NaHCO_3$ were then added with vigorous stirring. The mixture was allowed to react overnight. Unreacted glycols were removed from the polymer by repeated precipitations in methanol. The final non-cell binding comb copolymer had a molecular weight of approximately 40,000 Daltons, was insoluble in water, and incorporated approximately 40% by weight hydrophilic PEG side chains.

A pentamer amino acid sequence, Gly-Arg-Gly-Asp-Ser-Pro (GRGDSP from Gibco, referred to herein as RGD), was used to create adhesion ligand-bearing comb copolymers by tethering the RGD to functionalized ends of PEG side chains. RGD interacts specifically with receptors known as integrins on the surface of cell membranes, and RGD-integrin coupling mediates adhesion of cells to their surroundings in vivo. RGD was coupled to the non-cell binding comb copolymers via primary amines using known tresyl chloride chemistry (Obel, et al. *J. Polym. Sci. Polym. Lett. Ed.* 23:103 (1985)). Comb copolymers were activated with tresyl chloride groups in solution and stored at −20° C. until use. RGD was coupled to the combs by immersion in PBS solutions of RGD (25 μg/mL, pH 7.4) at 5° C. for 3 hours. Systems were multiply rinsed with PBS to remove unreacted RGD.

Film Processing

Mixtures of the activated comb copolymers and the non-cell binding comb copolymers were prepared in various ratios, and cast from solution in toluene onto glass slides. Films were subsequently dried under vacuum for 24 hours to remove residual solvent. RGD was subsequently subsequently coupled to the exposed activated comb polymers at the surface of the films in the manner described above. For mixtures containing 100 wt %, 25 wt % and 5 wt % tresyl-activated comb copolymer, surface RGD densities of 9.5 pg/cm$^2$, 2.5 pg/cm$^2$, and 0.5 pg/cm$^2$ were achieved, respectively.

Mixtures of polylactide, PLA, homopolymer and small amounts of the non-cell binding or RGD-bearing comb copolymers (10 wt % or less relative to PLA) were dissolved in toluene, and cast as films on glass. Films were subsequently dried under vacuum for 24 hours to remove residual solvent. Some of the comb/PLA films were subsequently annealed 96 hours in a 70° C. water bath. X-ray photoelectron spectroscopy studies showed significant enrichments of the comb copolymer at the surface of annealed blends (~60% by volume comb copolymer at the surface for a 10% bulk concentration). Advancing/receding contact angle measurements similarly indicate that the annealed blend films have substantially lower water contact angles than PLA and exhibit a large hysteresis indicative of PEG side chain reorientation/hydration at the surface when in contact with water.

Cell Culture

NR6 fibroblasts were cultured in serum-containing media onto the mixed comb films, the comb/PLA blends, and a PLA control film. Polymer films were first sterilized by immersion in ethanol. Wild-type NR6 fibroblasts were seeded on polymer film surfaces in Modified Eagle's Medium supplemented with fetal bovine serum. Cells were cultured for 24 hours, media was aspirated, and fresh media applied before phase contrast photomicrographs were taken.

Films of the non-cell binding combs were completely resistant to cell adhesion over 24 hour time periods, even in the presence of serum-supplemented medium. This is believed to be due to the formation of a dense hydrated layer of PEG side chains at the film surface. In the mixed comb films, increasing surface densities of RGD increased the adhesion and spreading of cells on the film surface. Variation in the weight fraction of RGD-coupled combs in films with unfunctionalized combs from 0 to 100% allowed a change in the adhesive response of cells to the surfaces. At 0% RGD-combs, no cells adhered, at 5% RGD-combs cells stuck but retained a rounded morphology, and at 100% RGD-combs cells were strongly adhered and spread on the surfaces. This result demonstrates that comb mixtures can provide some level of tunable ligand presentation and control over cell adhesion. The RGD-bearing surfaces supported cell adhesion and spreading even in the absence of serum. In addition, soluble RGD added to media abrogated the spreading of cells and detached them from the surfaces. These results indicate that the effects seen are due to specific interactions between cellular integrins and RGD and not interactions between integrins and serum proteins adsorbed on RGD.

On the surface of annealed PLA/non-cell binding comb blends, no cell adhesion was found due to the formation of the comb-enriched surface layer which resists protein adsorption. By comparison, cell adhesion was observed on unmodified PLA and, to a lesser degree, on the unannealed blend, which both allowed cells to stick and spread in an uncontrolled fashion. Cell culture studies on annealed PLA/RGD-bearing comb blends showed significant controlled cell attachment through the RGD ligands, even in the absence of serum.

Modulation of the degree of cell adhesion was also demonstrated in cell culture experiments with primary rat hepatocytes. The cells were plated at a density of 30,000 cell/cm$^2$ on substrates containing either 1% or 100% RGD-bearing comb in a 10% comb/PLA blend film, prepared and annealed as described above. Hepatocytes remain highly spread on substrates containing 100% RGD combs, but aggregate and assume a spheroidal morphology on blends in which only 1% of the combs were RGD-bearing.

Example 2

Preparation of Biodegradable Devices from Comb/PLA Blends

Porous Scaffold

Biodegradable PLA/comb copolymer microporous scaffolds that might be used as substrates for tissue engineering applications were prepared by freeze drying solutions of 10% wt/vol polymer in dioxane. Blends containing 10 wt % of the biodegradable, non-cell binding comb copolymer and 90 wt % PLA were dissolved in dioxane and frozen in liquid nitrogen, causing the phase separation of the polymer and solvent. Upon sublimating the dioxane, a porous biodegradable foam was obtained, which could be further treated, for example, by autoclaving or heat-treating in deionized (DI) water at 90° C., to achieve a high coverage of the comb copolymer on the pore exterior surfaces.

Temporary Barrier Membrane

Biodegradable PLA/comb copolymer microporous membranes that might be used as temporary barriers in wound healing applications were prepared by phase inversion casting from solutions of 10–20% polymer in N,N-dimethylformamide (DMF). Blends containing 10 wt % of the biodegradable, non-cell binding comb copolymer and 90 wt % PLA were dissolved in DMF and cast using a doctor blade onto a cleaned glass substrate. The substrate was immediately immersed in a bath of deionized (DI) water at 90° C. to create a porous membrane structure during the precipitation of the insoluble polymer. Once formed, the membranes were removed and rinsed in a second DI bath at 90° C. to remove trace solvent impurities.

Example 3

Preparation and Evaluation of Non-Biodegradable Comb Copolymers and Their Mixtures Comb Synthesis Non-biodegradable comb polymers were synthesized by free radical polymerization of methyl methacrylate (MMA) with either methoxy poly(ethylene glycol) methacrylate (MPEGMA) or poly(ethylene glycol) methacrylate (PEGMA) or a mixture of these initiated in toluene at 70° C. by azo(bis)isobutyronitrile. After 12–16 hours the reaction was terminated, and the polymer precipitated in petroleum ether. The resulting comb polymer has a PMMA backbone with PEO side chains nearly randomly distributed along the backbone, and a molecular weight of approximately 20,000 g/mole. The PEGMA macromonomers provide side chains end-capped with a hydroxyl group which can be derivatized for covalent linkage of the peptides, while the MPEGMA units provide non-reactive methoxy-terminated PEG side chains. Combs containing ~40% PEG side chains by weight are insoluble in water but form very hydrophilic, protein- and cell-resistant surfaces, and thus are considered non-cell binding.

To obtain adhesion ligand-bearing non-biodegradable combs, the RGD peptide was attached to hydroxyl end groups of the PEG side chains. The combs were dissolved in anhydrous tetrahydrofuran (THF), followed by addition of triethylamine and tresyl chloride, and reacted for 90 minutes. The activated polymer was recovered by precipitation in anhydrous methanol, and stored at $-70°$ C. until use. RGD was coupled through primary amines to the activated combs by first dissolving the combs in dry THF, followed by addition of peptide solution (1 mg/mL GRGDSP in phosphate buffered saline (PBS)) at a ratio of 10:1 THF:PBS. Coupling was allowed to proceed with stirring for 3 hours at 5° C. The resulting RGD-comb polymer was recovered by precipitation/washing with deionized water.

Film Preparation and Cell Culture

Films for cell culture were prepared by spin-coating the comb polymers onto glass substrates from anhydrous toluene. Purely cell-resistant surfaces were prepared by spin-coating solutions of the non-cell binding combs, while ligand-bearing surfaces were made by spin-coating solutions containing both non-cell binding combs and RGD-bearing combs.

NR6 fibroblasts transfected with the wild-type human epidermal growth factor receptor (WT NR6) were cultured in modified Eagle's medium alpha (MEM-α) supplemented with 7.5% fetal bovine serum, L-glutamine, non-essential amino acids, sodium pyruvate, penicillin-streptomycin, and gentamycin antibiotic. Cell were seeded at 20,000 cells/cm$^2$ onto comb copolymer films for 24 hours, followed by aspiration to remove unattached cells and application of fresh medium. Morphology/adhesion of cells to films was then assessed using a Zeiss Axiovert 100 phase contrast microscope. No cell adhesion was observed on films of non-cell binding combs. In contrast, films of the RGD-bearing combs supported adhesion and produced cell morphologies comparable to that observed on fibronectin.

Example 4

Preparation and Evaluation of EGF-Tethered Comb Films

Film Preparation

To obtain non-biodegradable combs with tethered epidermal growth factor ligands, non-cell binding combs with PMMA backbones and PEG side chains were prepared as described in Example 3. EGF was attached to hydroxyl end groups of the PEG side chains by first activating the side chains with tresyl chloride following the procedure described above.

Films of the tresyl-activated comb were spin-coated at 1000 rpm from 0.01 g/ml toluene solutions. Films were subsequently dried under vacuum to remove residual solvent, then sterilized by UV exposure for 1 hour. EGF was coupled to surfaces by incubating 5 μg/ml sterile PBS solutions (100 mM phosphate) of EGF on the films for 3 hours at 5° C. Solutions were aspirated and samples were blocked with 100 mM pH7 sterile tris solutions 1 hour at 20° C. Controls were hydrolyzed in the presence of tris, thereby capping all the tresyl sites with tris instead of EGF. One hydrolyzed control was exposed to an EGF solution under conditions simulating the EGF coupling step to check for nonspecific adosrption of EGF: Samples were multiply rinsed with sterile PBS. This protocol provided 1.0±0.3 ng/cm$^2$ tethered EGF on the film surface.

Cell Culture

PC12 cells were seeded (medium: RMPI 1640 with 5% FBS, 10% horse serum heat-inactivated donor herd, and supplemented with pennicilin-streptomycin) on surfaces and cultured 3 days. To keep the PC12 cells attached to the surface in this experiment, prior to culturing, surfaces were exposed to 0.5 mg/mil rat tail collagen solutions overnight at 5° C. PC12s are an adrenyl tumor cell type which differentiates into a neuronal phenotype under certain conditions. This differentiation is similar to that of neuronal cells in general, morphologically characterized by the formation and extension of neurites. PC12 cells cultured in the presence of soluble EGF are reported to undergo a morphological change induced by the growth factor signal- cells round up on adhesive surfaces, likely due either to down-regulation of integrins or changes in integrin-ECM affinity induced by EGF signals. The EGF-bearing comb films are non-adhesive to cells and the collagen treatment leads to only weakly cell-adhesive surfaces. PC12 cells were cultured as described for several weeks. At 3 days initial evidence of differentiation was observed, which became very clear after two weeks. No differentiation was observed on controls.

Example 5

Preparation of Surfaces Presenting Multiple Ligand Types

Non-cell binding comb copolymers with PEA backbones and methoxy- or hydroxyl-terminated PEO side chains were prepared as described in Example 3. The combs were subsequently used to create substrates which present co-tethered epidermal growth factor (EGF) and RGD. First, RGD-bearing combs were prepared in the manner described in Example 3. The RGD-bearing combs were solvated in THF along with non-cell binding combs activated with tresyl chloride, and films were cast onto cleaned glass substrates using standard spin-coating procedures. Films were dried under vacuum for 24 hrs to remove remaining solvent. The substrate was then exposed to an EGF solution, enabling the covalent attachment of EGF to the activated comb side chains at the surface through the terminal amine group of the EGF. Solutions of 10 ng/mL EGF in PBS were incubated on surfaces containing the activated combs mixed with the RGD combs, or with controls containing unactivated combs. The amount of EGF covalently linked to the substrates under these conditions was 8.5±1.5 ng/cm$^2$. For comparison, maximum DNA synthesis response in primary rat hepatocytes cultured on tethered EGF occurred at a density of less than 1 ng/cm$^2$ (1000 EGF molecules/μm$^2$) and the approximate density of receptors on the cell surface of hepatocytes or WT NR6 is 100–400 molecules/μm$^2$. Thus the amount of EGF which can be covalently linked on the RGD-bearing substrate is sufficient for influencing cell response. Further, the amount of non-specifically adsorbed EGF on the comb surfaces, 0.9±0.3 ng/cm$^2$, is negligible relative to the amount that is covalently coupled. WT NR6 fiberblasts were cultered for 24 hours as previously described on the EGF/RGD substrates. Cells were observed to adhere and spread on the nixed ligand surface.

Example 6

Comb Copolymer-Stabilized Latexes

Comb Synthesis

Comb polymer stabilizer was synthesized free-radically in solution Methyl methlacrylate (MMA), methoxy poly (ethylene glycol) methacrylate (MPEGMA), and poly (ethylene glycol) methacrylate (PEGMA) were added to benzene in equal weight fractions of the two PEG macromonomers, for a total monomer concentration of 0.6 M. Azo(bis)iso-butyronitrite was added at a molar ratio of 20:1 [monomer]:[initiator]. The solution was degassed under nitrogen 15 minutes, followed by polymerization at 60° C. for 16 hours. The comb polymer was purified by repeated precipitation in petroleum ether. In order to obtain latex beads with protein-resistant surfaces, the ratio of PEGMA/MPEGMA units to MMA units in the comb stabilizer copolymers was first optimized. Initial studies found that combs containing 40 wt % of the PEGMA/MPEGMA units formed films that were cell resistant in the presence of serum and simultaneously resistant to dissolution in water-based media. Combs of this composition were soluble in 50/50 water/ethanol, and thus served as an ideal stabilizer for preparation of the polymer latexes. Combs with greater PEG fractions (~50 wt % or more) were water soluble over time. The comb stabilizer had a total molecular weight, prior to peptide attachment, of approximately 23,000 Daltons.

To obtain adhesion ligand-bearing latexes, RGD-bearing combs were first prepared by solution coupling GRGDSP (Gibco) to the ends of the PEGMA units of the comb. Coupling was accomplished through the reaction of tresyl chloride-activated combs and the N-terminal amine of the peptide. The hydroxyl ends of the PEGMA units of the comb were activated by reaction with 2,2,2-trifluoroethanesulfonyl chloride (tresyl chloride) in tetrahydrofuran. The comb copolymer (150 mg) was dissolved in 25 ml dry THF at 5° C. Triethylamine (200 $\mu$l) and tresyl chloride (250 $\mu$l) were added and the reaction was allowed to proceed 3 hours. The activated polymer was then recovered by filtration and precipitation in petroleum ether. GRGDSP peptide was coupled to the activated polymer by adding 150 $\mu$l GRGSP solution (1 mg/ml in pH 7.4 phosphate buffered saline) to 2.5 ml of activated comb solution (0.02 g/ml in THF) at 5° C. and stirring for 3 hours. The RGD-coupled comb was recovered by overnight precipitation in deionized water. Amounts of peptide coupled were determined by a colorimetric assay (microBCA, Pierce Chemical Co.). RGD content was found to be 0.3 wt % (1 RGD peptide per~10 comb polymer molecules).

Acrylic Latex Syntheses

Methacrylate- and acrylate-based polymer latexes were synthesized by dispersion polymerization employing the comb polymers as stabilizing agents. Latexes of four different compositions were prepared in this study: pure poly (methyl methacrylate), poly(methyl methacrylate-co-butyl acrylate), poly(ethyl methacrylate-co-methyl acrylate), and poly(ethyl methacrylate-co-butyl methacrylate). In addition, one cell-interactive poly(methyl methacrylate) latex was prepared using the RGD-comb stabilizer. Comb stabilizer was dissolved in a 1:1 mixture by volume of ethanol and water, followed by addition of methacrylate/acrylate monomers and 0.57 g ammonium persulfate. Reactions were allowed to proceed 18 hours at 60° C. with stirring. Reactions began as one phase, clear solutions, and became opaque white dispersions during polymerization. After completion of the syntheses, all latexes were purified by repeated centrifugation and redispersion in water/ethanol. Suspensions were stable over greater than 24 hour periods and could be resuspended after extended storage via ultrasonic mixing. All latexes were ultrasonically treated for at least 30 minutes prior to use. Molecular weights of the polymers comprising the latex particles ranged from approximately 400,000 Daltons to 1 millon Daltons. Glass transition temperatures of the particles ranged from −26° C. to 105° C., depending on the monomer constituents used in the polymerization.

Morphology of the latex beads was assessed by examining beads cast on substrates using a JEOL 6320 field emission scanning electron microscope operating at a 4.0 kV accelerating voltage. Samples were shadowed with gold prior to imaging. Average particle diameters were measured from SEM micrographs, with at least 300 particles measured for each sample. Average particle sizes ranged from 0.2 to 1.8 micrometers. All of the latexes had size polydispersities below 1.06. In each case, the comb stabilizer comprised below 1 wt % of the total latex bead composition.

Latex Film Preparation and Characterization

Films were prepared from the latex suspensions by spin-coating the particles (0.02–0.03 g/ml in water/ethanol) at 1000 rpm onto cleaned glass substrates. To form contiguous films from the cast particles, short heat treatments (30–60 seconds) were applied to the samples by a heat gun set at 800–900° C. Coalescence of the particles was confirmed by examining, the surfaces in a light microscope. For cell culture and contact angle experiments, poly(methyl methacrylate) homopolymer (not a latex) served as a control substrate. PMMA (Polysciences, 68K g/mole, $M_w/M_N$= 1.07) films were spincoated from a 0.03 g/ml toluene solution onto clean glass coverslips at 1000 rpm, followed by drying in vacuo at 70° C. 24 hours.

Contact angles of water on coalesced latex film surfaces, films of the non-cell binding comb, and on the PMMA control film were measured using a VCA2000 video contact angle system (AST Inc.). Advancing/receding contact angles were measured by capturing digital images of deionized water droplets placed by syringe on virgin surfaces and measuring angles from the images. In all cases but the control, the advancing contact angles are seen to be relatively constant and independent of drop volume, while the receding angles show significant changes in contact angle with drop size. All of the latex films showed hysteresis of 25° or more in these measurements, while pure PMMA displayed only a ~10° change. Though contact angle hysteresis can occur for a number of reasons, the likeliest explanation for the contact angle hysteresis observed here is the reorganization/hydration of the PEG side chains at the surface of the films upon wetting. That the comb copolymer is not water-soluble was confirmed by ellipsometry measurements of dried latex and comb film thicknesses before and after water immersion, which showed no detectable loss of polymer. These results provide a strong indication that the comb stabilizer remains at the surface once the latex particles coalesce into a homogeneous film.

Cell Culture

All cell culture reagents were purchased from Gibco. NR6 fibroblasts transfected with the wild-type human epidermal growth factor receptor (WT NR6) were cultured in modified Eagle's medium alpha (MEM-$\alpha$) supplemented with 7.5% fetal bovine serum, L-glutamine, non-essential amino acids, sodium pyruvate, penicillin-streptomycin, and gentamycin antibiotic.

Cell attachment studies were performed by seeding 20,000 cells/$cm^2$ onto the non-cell binding comb copolymer films, coalesced PMMA latex films, and two controls: tissue culture polystyrene (TCPS) and pure PMMA films. Cell were seeded in 1.5 ml serum-containing growth medium for 24 hours, followed by aspiration to remove unattached cells and application of fresh medium. Morphology/adhesion of cells to latex films was then assessed using a Zeiss Axiovert 100 phase contrast microscope.

After 24 hours, cells are attached and spread on both controls, presumably via protein layers adsorbed onto these surfaces. However, the PEG side chains of the comb copolymer stabilizer provide complete cell resistance for the comb film under these stringent conditions. Likewise, the PMMA latex film presents a surface with essentially equivalent cell-resistant capacity, although the comb stabilizer comprises only ~1 wt % of the total polymer film. This observation is further evidence that the combs remain localized to the film surface during coalescence.

Films coalesced from the RGD-bearing PMMA latex were prepared and seeded with WT NR6 cells as before. In contrast to latexes stabilized with the non-cell binding combs, coalesced films of the RGD-bearing latex elicited cell attachment and spreading. Apparently, surface densities of RGD ligand obtained for these latex films are comparable to the pure RGD-linked comb, although the latex film contains 1/100 as much total peptide. Specificity of the adhesion of cells to the RGD-bearing surface was confirmed by adding excess soluble GRGDSP (45 mM) lo the culture media. All cells were observed to detach within 1 hour of soluble RGD administration.

Modifications and variations of the present invention will be obvious to those skilled in the art from the foregoing detailed description. Such modifications and variations are intended to come within the scope of the following claims.

We claim:

1. A method for engineering tissue comprising growing cells on a tissue-engineering matrix formed of or coated with the cell-regulating, comb-type copolymer comprising:
   a) a hydrophobic polymer backbone;
   b) non-cell binding hydrophilic polymeric side chains grafted to the polymer backbone, wherein the side chains have a molecular weight between 200 and 2000 Daltons;
   wherein between zero and 100% of the non-cell binding, hydrophilic side chains are end-capped with cell-binding or cell-signaling ligands to form short cell-binding copolymer side chains and
   wherein the side chains comprise less than 60% of the total copolymer weight,
   wherein the comb copolymer is effective in regulating cellular adhesion or response to the surface.

2. A polymer latex comprising polymer particles dispersed in aqueous-containing media stabilized by cell-regulating, comb-type copolymer comprising:
   a) a hydrophobic polymer backbone;
   b) non-cell binding hydrophilic polymeric side chains grafted to the polymer backbone, wherein the side chains have a molecular weight between 200 and 2000 Daltons;
   wherein between zero and 100% of the non-cell binding, hydrophilic side chains are end-capped with cell-binding or cell-signaling ligands to form short cell-binding copolymer side chains and
   wherein the side chains comprise less than 60% of the total copolymer weight.

3. The polymer latex of claim 2 wherein the comb copolymers serve as a stabilizing agent during the latex synthesis.

4. The polymer latex of claim 2 whereby the comb copolymer comprises less than 1% of the latex dry weight.

5. The polymer latex of claim 2 further comprising non-cell-binding comb copolymers whose side chains are not end-capped with cell-binding or cell-signaling ligands.

6. The polymer latex of claim 2 further comprising latex particles stabilized by non-cell binding comb copolymers to achieve a defined mixture of non-cell binding and ligand-modified cell-regulating latex particles.

7. The polymer latex of claim 2 in which non-cell binding side chains of the comb copolymers at the surface of the particles are end-capped with ligands after the latex particles are synthesized.

8. Polymer coatings and films that regulate cell behavior prepared by casting a polymer latex comprising polymer particles dispersed in aqueous-containing media stabilized by cell-regulating, comb-type copolymers comprising:
   a) a hydrophobic polymer backbone;
   b) non-cell binding hydrophilic polymeric side chains grafted to the polymer backbone, wherein the side chains have a molecular weight between 200 and 2000 Daltons;
   wherein between zero and 100% of the non-cell binding, hydrophilic side chains are end-capped with cell-binding or cell-signaling ligands to form short cell-binding copolymer side chains and
   wherein the side chains comprise less than 60% of the total copolymer weight.

9. The polymer films and coatings of claim 8 prepared by casting a mixed latex of microparticles stabilized with the non-cell binding comb copolymers to achieve a defined mixture of non-cell binding and ligand-modified cell-regulating latex particles.

10. The polymer films and coatings of claim 8 comprising discrete domains of a single type of cell-signaling ligand against a background of non-cell binding hydrophilic side chains, where the domain size is on the order of the latex particles.

11. The polymer films and coatings of claim 10 wherein the domain size is between 0.1 and 10 microns in diameter.

12. The polymer films and coatings of claim 8 comprising discrete domains of multiple cell-signaling ligands against a background of non-cell binding hydrophilic side chains, wherein the domain size is on the order of the latex particles.

13. The polymer films and coatings of claim 12 where the domain size is between 0.1 and 10 microns in diameter.

14. The polymer film or coating of claim 8 in which non-cell binding side chains of the comb copolymers at the surface of the applied film or coating are end-capped with ligands after the coating or film is prepared.

15. A method of making polymer coatings and films that regulate cell behavior comprising casting a polymer latex comprising polymer particles dispersed in aqueous-containing media stabilized by cell-regulating, comb-type copolymers comprising:
   a) a hydrophobic polymer backbone;
   b) non-cell binding hydrophilic polymeric side chains grafted to the polymer backbone, wherein the side chains have a molecular weight between 200 and 2000 Daltons;
   wherein between zero and 100% of the non-cell binding, hydrophilic side chains are end-capped with cell-binding or cell-signaling ligands to form short cell-binding copolymer side chains and
   wherein the side chains comprise less than 60% of the total copolymer weight.

16. The method of making polymer film or coatings of claim 15 wherein non-cell binding side chains of the comb copolymers at the surface are end-capped with ligands after the coating or film is prepared.

* * * * *